(12) United States Patent
Suzuki et al.

(10) Patent No.: US 9,155,914 B2
(45) Date of Patent: Oct. 13, 2015

(54) COMPOSITION FOR EXTERNAL APPLICATION TO SKIN

(75) Inventors: Yasuto Suzuki, Haga-gun (JP); Kazue Tsukahara, Haga-gun (JP)

(73) Assignee: Kao Corporation, Tokyo (JP)

(*) Notice: Subject to any disclaimer, the term of this patent is extended or adjusted under 35 U.S.C. 154(b) by 866 days.

(21) Appl. No.: 12/742,525

(22) PCT Filed: Nov. 5, 2008

(86) PCT No.: PCT/JP2008/070140
§ 371 (c)(1),
(2), (4) Date: May 12, 2010

(87) PCT Pub. No.: WO2009/063782
PCT Pub. Date: May 22, 2009

(65) Prior Publication Data
US 2010/0273875 A1    Oct. 28, 2010

(30) Foreign Application Priority Data
Nov. 13, 2007 (JP) ................................ 2007-294763

(51) Int. Cl.
| A61K 8/42 | (2006.01) |
|---|---|
| A61K 8/41 | (2006.01) |
| A61Q 19/08 | (2006.01) |
| A61K 31/131 | (2006.01) |
| A61K 31/16 | (2006.01) |
| A61K 31/22 | (2006.01) |
| A61K 31/23 | (2006.01) |

(52) U.S. Cl.
CPC . *A61Q 19/08* (2013.01); *A61K 8/41* (2013.01); *A61K 8/416* (2013.01); *A61K 8/42* (2013.01); *A61K 31/131* (2013.01); *A61K 31/16* (2013.01); *A61K 31/22* (2013.01); *A61K 31/23* (2013.01)

(58) Field of Classification Search
None
See application file for complete search history.

(56) References Cited

U.S. PATENT DOCUMENTS

| 5,082,866 | A | 1/1992 | Wong et al. | |
|---|---|---|---|---|
| 5,562,898 | A | 10/1996 | Dowell et al. | |
| 5,961,999 | A * | 10/1999 | Bimczok et al. | 424/401 |
| 6,335,368 | B1 | 1/2002 | Liviero et al. | |
| 6,414,028 | B1 * | 7/2002 | Buyuktimkin et al. | 514/573 |
| 7,205,003 | B2 | 4/2007 | Maibach et al. | |
| 2003/0099678 | A1 * | 5/2003 | Maibach et al. | 424/401 |
| 2007/0197420 | A1 | 8/2007 | Antoine et al. | |

FOREIGN PATENT DOCUMENTS

| DE | 1163850 | B2 | 2/1964 | | |
|---|---|---|---|---|---|
| DE | 217513 | A1 | 1/1985 | | |
| DE | 3339196 | | * 5/1985 | | |
| EP | 327379 | A2 | 8/1989 | | |
| JP | 1985-184005 | | 9/1985 | | |
| JP | 60184005 | | * 9/1985 | ............... | A61K 7/00 |
| JP | 1990-160714 | | 6/1990 | | |
| JP | 02160714 | | * 6/1990 | ............... | A61K 7/08 |
| JP | A-2-160714 | | * 6/1990 | | |
| JP | 6-9334 | A | 1/1994 | | |
| JP | 8-333217 | A | 12/1996 | | |
| JP | 2002-514586 | A | 5/2002 | | |
| JP | 2004-514646 | A | 5/2004 | | |
| JP | P3549823 | | 8/2004 | | |
| JP | 2005-528323 | | 9/2005 | | |
| WO | WO 99/58106 | | 11/1999 | | |
| WO | WO 01/17486 | | * 3/2001 | ............... | A61K 7/00 |
| WO | WO 01/17486 | A2 | 3/2001 | | |
| WO | WO 03/026680 | A2 | 4/2003 | | |
| WO | WO 2005/121291 | A1 | 12/2005 | | |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802.*
International Search Report for PCT/JP2008/070140, mailed Dec. 2, 2008 from the Japanese Patent Office, Tokyo, Japan.
Malka, D. et al., "Acute hepatitis caused by alverine associated with anti-lamin A and C autoantibodies," *J. Hepatology* 27:399-403 (1997), European Assoc. for the Study of the Liver, Geneva, Switzerland.
Dialog Database, Derwent World Patent Index File 351 Accession No. 10651997, English language abstract and patent family for JP 3549823, published Aug. 4, 2004.
International Preliminary report on Patentability (Chapter I), including the Written Opinion for PCT/JP2008/070140, translation mailed Jun. 29, 2010 from the International Bureau of WIPO, Geneva, Switzerland.
Extended European search report, including the Supplementary European search report and the European search opinion, for EP Appl. No. 08848873.9, dated Jun. 23, 2015, European Patent Office, Munich, Germany.

* cited by examiner

*Primary Examiner* — Dennis Heyer
(74) *Attorney, Agent, or Firm* — Sterne, Kessler, Goldstein & Fox P.L.L.C.

(57) ABSTRACT

A composition for external application to skin, containing a compound represented by formula (I) or a salt thereof, and/or a quaternary ammonium salt represented by formula (II):

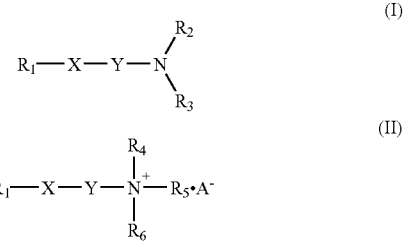

wherein $R_1$ is a substituted or unsubstituted, linear or branched chain alkyl group having 2 to 25 carbon atoms; X is —CO—NH—, —O—CO—O—, —NH—CO—, —CO—O—, —O—CO— or —O—; Y is a substituted or unsubstituted alkylene group having 1 to 4 carbon atoms; $R_2$ is a hydrogen atom or an alkyl group having 1 to 4 carbon atoms; $R_3$ is an alkyl group having 1 to 4 carbon atoms; $R_2$ and $R_3$ are the same as or different from each other; $R_4$, $R_5$ and $R_6$, which may the same as or different from each other, each are an alkyl group having 1 to 4 carbon atoms; and $A^-$ is a counter ion.

10 Claims, 5 Drawing Sheets

COMPOSITION FOR EXTERNAL APPLICATION TO SKIN

TECHNICAL FIELD

The present invention relates to a composition for external application to skin.

BACKGROUND ART

Examples of appearance changes caused by skin aging include formation of wrinkles and sagging and reduction of skin firmness. Until now, cosmetics containing, for example, collagen have been used for improving such appearance changes of the skin. However, even if such cosmetics are used, the effect of inhibiting (suppressing) wrinkle formation or the like is insufficient.

Formation of wrinkles or the like is considered to have a strong association with ultraviolet rays. Skin aging caused by irradiation with ultraviolet rays is referred to as "photoaging", and a variety of studies have been made. However, the present situation resides in that a cosmetic, which can be used as an alternative of an ultraviolet absorber or an ultraviolet protectant in order to prevent the photoaging, has not yet been developed.

On the other hand, Japanese Patent No. 3549823 discloses an agent which contains alverine and is useful for reducing wrinkles and fine wrinkles. Specifically, Japanese Patent No. 3549823 discloses that alverine can induce a decontraction and/or relaxant effect in the striated muscle, and the effect can repair wrinkles and fine wrinkles and promote smoothing of the skin. However, alverine is used as a muscle relaxant in Europe based on its acetylcholine-blocking action. Alverine has been used as a drug and has high toxicity (refer to, for example, David Malka et al., Journal of Hepatology, 1997, vol. 27, p. 399-403).

Moreover, JP-A-2005-528323 ("JP-A" means unexamined published Japanese patent application) and JP-A-08-333217 disclose agents for external application to skin which are used for improving and preventing appearance changes such as wrinkles of the skin. The agents for external application to skin described in the documents can improve and suppress epidermal wrinkles (for example, wrinkles caused by drying) due to aging of epidermal cells of the skin. However, the effect for deep and stubborn wrinkles produced in dermal cells or cell tissues located deeper than the dermal cells is insufficient.

As described above, a photoaging-preventing or -improving composition or a wrinkle-preventing or -improving composition, which can be used safely and has a sufficient effect, has not been known.

DISCLOSURE OF INVENTION

The present invention relates to a composition for external application to skin which can be used as a photoaging-preventing or photoaging-improving composition or a wrinkle-preventing or wrinkle-improving composition.

The inventors of the present invention have made extensive studies to solve the above-mentioned problems, and as a result, the inventors have found out that a specific compound has an activity for improving and/or preventing photoaging and an activity for improving and/or preventing wrinkles. The present invention has been completed based on the finding.

The present invention relates to a composition for external application to skin, comprising a compound represented by formula (I) or a salt thereof, and/or a quaternary ammonium salt represented by formula (II):

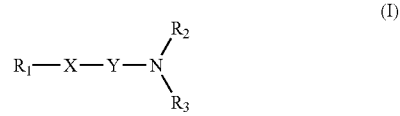
(I)

wherein $R_1$ is a substituted or unsubstituted, linear or branched chain alkyl group having 2 to 25 carbon atoms; X is —CO—NH—, —O—CO—O—, —NH—CO—, —CO—O—, —O—CO— or —O—; Y is a substituted or unsubstituted alkylene group having 1 to 4 carbon atoms; $R_2$ is a hydrogen atom or an alkyl group having 1 to 4 carbon atoms; $R_3$ is an alkyl group having 1 to 4 carbon atoms; and $R_2$ and $R_3$ are the same as or different from each other; and

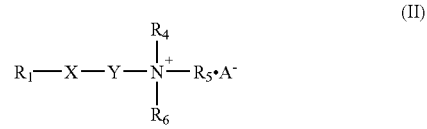
(II)

wherein $R_1$, X and Y have the same meaning as those in formula (I), respectively; $R_4$, $R_5$ and $R_6$, which may the same as or different from each other, each are an alkyl group having 1 to 4 carbon atoms; and $A^-$ is a counter ion.

In addition, the present invention relates to a method for preventing photoaging and/or improving photoaging, comprising applying the composition for external application to skin.

Other and further features and advantages of the invention will appear more fully from the following description, appropriately referring to the accompanying drawings.

BEST MODE FOR CARRYING OUT THE INVENTION

Figure 1:
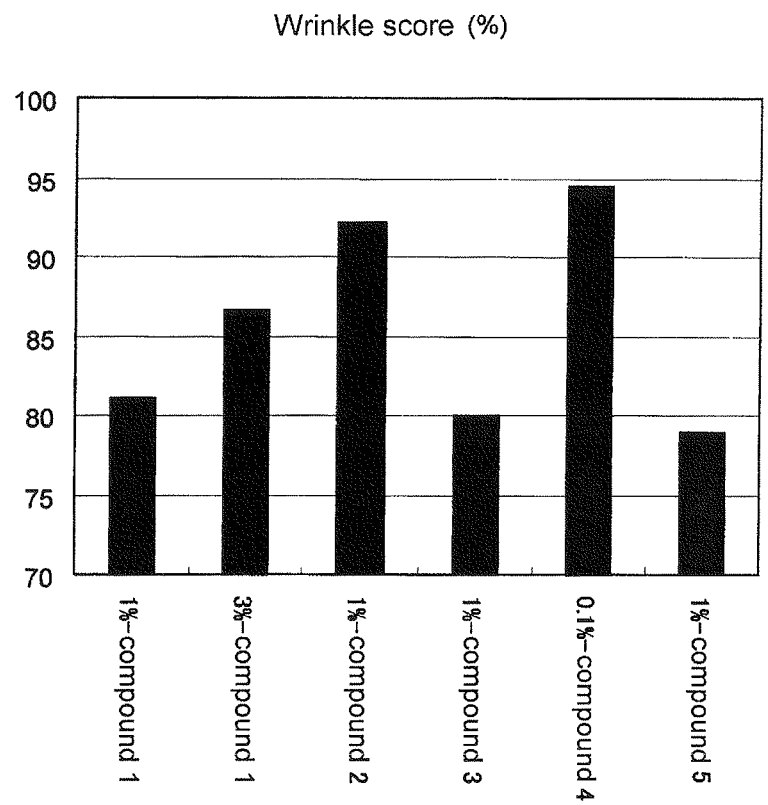
FIG. 1 is a graph illustrating the results of evaluation of wrinkle-preventing effect (visual evaluation of wrinkles) in Example 1.

Hereinafter, the present invention is described in detail based on preferred embodiments of the invention.

The composition for external application to skin according to the present invention contains a compound represented by the above formula (I) or a salt thereof and/or a quaternary ammonium salt represented by the above formula (II). The composition for external application to skin according to the present invention has an effect of preventing or improving wrinkles formed by damages in a dermal tissue or a tissue located deeper than the dermal tissue and has an action of preventing or improving appearance changes (such as wrinkles and sagging) or reduction of skin firmness, which are both caused by skin aging. In particular, the composition for external application to skin according to the present invention can act on photoaging and has an excellent action of preventing or improving wrinkles due to photoaging. Herein, the term "photoaging" refers to skin aging caused by irradiation with ultraviolet rays (for example, formation of sagging or reduction of skin firmness).

Examples of the substituted or unsubstituted, linear or branched alkyl group having 2 to 25 carbon atoms represented by $R_1$ in the above formula (I) or (II) include an ethyl group, an n-propyl group, an i-propyl group, an n-butyl group, an i-butyl group, a sec-butyl group, a t-butyl group, an n-pentyl group, an n-hexyl group, a 2-ethylhexyl group, an n-heptyl group, an n-octyl group, an n-nonanyl group, an n-decyl group, a trimethyldecyl group, an n-undecyl group, an n-dodecyl group, an n-tridecyl group, an n-tetradecyl group, an n-pentadecyl group, an n-hexadecyl group, an n-heptadecyl group, an n-octadecyl group, a methylheptadecyl group (methyl-branched isostearyl group), an n-nonadecyl group, an n-icosyl group, an n-henicosasyl group, an n-docosanyl group, an n-tricosanyl group, an n-tetracosanyl group, and an n-pentacosanyl group. In particular, preferred is a substituted or unsubstituted, linear or branched alkyl group having 6 to 20 carbon atoms such as an n-hexyl group, a 2-ethylhexyl group, an n-heptyl group, an n-octyl group, an n-nonanyl group, an n-decyl group, a trimethyldecyl group, an n-undecyl group, an n-dodecyl group, an n-tridecyl group, an n-tetradecyl group, an n-pentadecyl group, an n-hexadecyl group, an n-heptadecyl group, an n-octadecyl group, a methylheptadecyl group (methyl-branched isostearyl group), an n-nonadecyl group, and an n-icosyl group, more preferred is a substituted or unsubstituted, linear or branched alkyl group having 8 to 18 carbon atoms, still more preferred is an unsubstituted, linear alkyl group having 10 to 14 carbon atoms, and particularly preferred is an unsubstituted, linear alkyl group having 11 or 12 carbon atoms.

In formula (I) or (II), X is —CO—NH—, —O—CO—O—, —NH—CO—, —CO—O—, —O—CO— or —O—. In particular, it is preferable that X is —CO—NH—, —NH—CO—, —CO—O— or —O—CO—.

Examples of the substituted or unsubstituted alkylene group having 1 to 4 carbon atoms represented by Y in the above formula (I) or (II) include a methylene group, an ethylene group, a propylene group, and a butylene group. Particularly preferred is a methylene group or an ethylene group.

Examples of the alkyl group having 1 to 4 carbon atoms represented by $R_2$ and $R_3$ in the above formula (I) and $R_4$, $R_5$, and $R_6$ in the above formula (II) include a methyl group, an ethyl group, a propyl group, and a butyl group. In particular, it is preferred that an alkyl group having 1 to 4 carbon atoms represented by $R_2$ and $R_3$ in the formula (I) be a methyl group or an ethyl group. It is preferred that an alkyl group having 1 to 4 carbon atoms represented by $R_4$, $R_5$, and $R_5$ in the formula (II) be a methyl group or an ethyl group.

The alkyl group having 2 to 25 carbon atoms represented by $R_1$ and the alkylene group having 1 to 4 carbon atoms represented by Y in the above formula (I) or (II) may each undergo substitution with one or more substituents. Examples of the substituents include a halogen atom, a hydroxyl group, an alkoxyl group, an acyl group, an amino group which may be protected, a carboxyl group which may be protected, and a heterocyclic group, and are not particularly limited. Here, examples of the halogen atom include a chlorine atom, a bromine atom, and an iodine atom. An alkoxyl group having 1 to 12 carbon atoms is preferred as the alkoxyl group, and examples thereof include a methoxy group, an ethoxy group, and an isopropoxy group. An alkanoyl group having 1 to 12 carbon atoms is preferred as the acyl group, and examples thereof include a formyl group, an acetyl group, a propionyl group, and a butyryl group. Examples of the amino group which may be protected include an amino group, an acylamino group, an alkylamino group, and a dialkylamino group. Examples of the carboxyl group which may be protected include a carboxyl group and an alkoxycarbonyl group. The heterocyclic group is, for example, preferably a 5- to 14-membered monocyclic or fused ring group having 1 to 3 nitrogen atoms, oxygen atoms, and/or sulfur atoms as hetero atoms. Examples thereof include a pyridyl group, a pyridazinyl group, a furyl group, a thienyl group, an indolyl group, a thiazolyl group, an imidazolyl group, a benzofuryl group, and a benzothienyl group.

Examples of the counter ion represented by $A^-$ in the above formula (II) include a halogen ion, a carboxylate ion, a sulfonate ion, a sulfate ion, and a nitrate ion. In particular, preferred area halogen ion and a carboxylate ion. Examples of the halogen ion include a fluorine ion, a chlorine ion, a bromine ion, and an iodine ion, and are not particularly limited. Examples of the carboxylate ion include a formylate ion, an acetylate ion, a propylate ion, a fumarate ion, and a maleate ion, and are not particularly limited.

Examples of the salt of the compound represented by the above formula (I) include salts with inorganic acids such as hydrochloric acid, sulfuric acid, phosphoric acid, hydrobromic acid, hydroiodic acid, nitric acid, pyrosulfuric acid, and metaphosphoric acid; salts with organic acids such as citric acid, benzoic acid, acetic acid, propionic acid, fumaric acid, maleic acid, and sulfonic acid (for example, methanesulfonic acid, p-toluene sulfonic acid, and naphthalene sulfonic acid); and salts with amino acids such as glutamic acid and aspartic acid.

In particular, as the compound represented by the above formula (I), preferred are 2-dimethylamino-ethyl dodecanoate, 2-dimethylamino-N-dodecyl-acetamide, dodecyl dimethylamino acetate, (2-dodecyloxy-ethyl)-dimethylamine, and (2-dimethylaminoethyl)amide dodecanoate.

The compound represented by the above formula (I) or a salt thereof, and the quaternary ammonium salt represented by the formula (II) may be produced through the method described in, for example, Izv. Vyssh. Ucheb. Zaved., Khim. Khim. Tekhnol., 14(9), 1369 (1971) by, for example, reacting choline chloride with fatty acid chloride under a nitrogen stream.

Hereinafter, preferred specific examples of the compound represented by formula (I) or a salt thereof, and the quaternary ammonium salt represented by formula (II) will be shown, but the present invention should not be limited thereto. In the following specific examples, "Me" represents a methyl group, and "Et" represents an ethyl group.

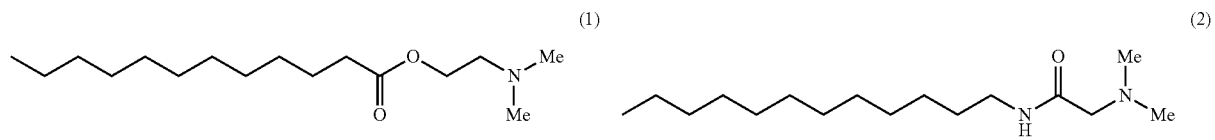

-continued

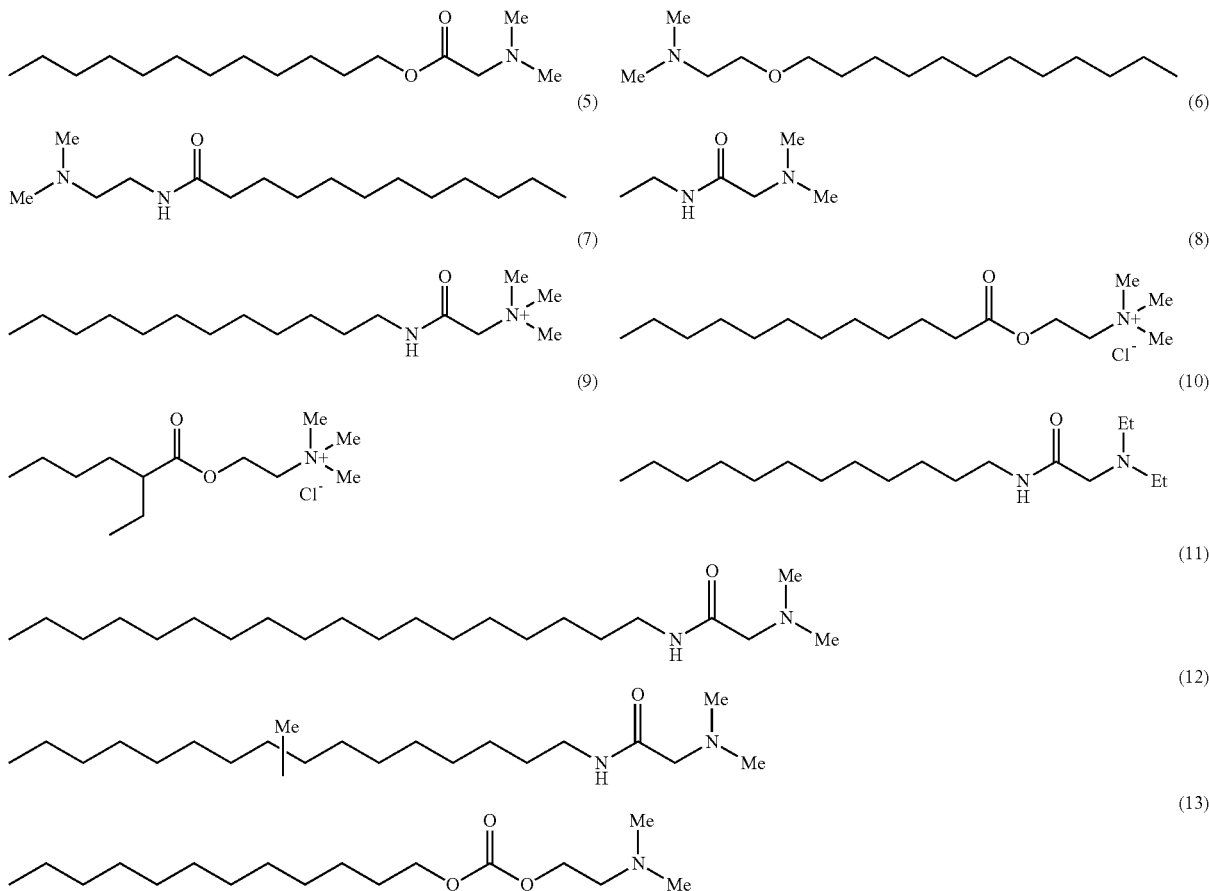

The composition for external application to skin according to the present invention may appropriately contain, in addition to the compound represented by formula (I) or a salt thereof, and/or the quaternary ammonium salt represented by formula (II), a variety of ingredients or carriers which are usually employed in cosmetics, quasi-drugs, drugs or the like. Examples of such ingredients or carriers include humectants, powders, gelation agents, thickeners, surfactants, emulsifiers, anti-inflammatory agents, antioxidants, pH regulating agents, chelating agents, preservatives, thickeners, dyes, perfumes. UV absorbing agents. UV protecting agents, and existing skin-aging preventive or retarding agents such as collagen. The composition may be produced through a conventional method in accordance with the solvent to be used, the application form or the like.

The solvent which may be used for the composition for external application to skin according to the present invention is not particularly limited, and examples of the solvent include: lower alcohols having 1 to 4 carbon atoms such as ethanol and isopropyl alcohol; and polyvalent alcohols such as propylene glycol and glycerin.

The application form of the composition for external application to skin according to the present invention includes pharmaceutical compositions for external application and cosmetic compositions.

Examples of pharmaceutical compositions for external application include a variety of ointments containing a pharmaceutically active ingredient. Such an ointment may comprise an oily base, or an oil-in-water or water-in-oil emulsion base. Examples of the oily base include vegetable oil, animal oil, synthetic oil, fatty acid, and natural or synthetic glyceride. Examples of the pharmaceutically active ingredient include anti-inflammatory agents, antipruritic drugs, astringent agents, and hormones.

Examples of cosmetic compositions include lotions, emulsions, creams, ointments, sticks, solutions in organic solvents or purified water, packs, gels and aerosols. Namely, the cosmetic composition may be employed as a lotion, an oil essence, an O/W-type (oil-in-water type) or W/O-type (water-in-oil type) cream, a pack, a foundation, a skin lotion, a skin-cleansing agent, a tonic, a bathing agent, an aerosol, a gel or the like.

The compound represented by formula (I) or a salt thereof, and/or the quaternary ammonium salt represented by formula (II) is incorporated into the composition for external application to skin according to the present invention in an amount of, for example, 0.0001 to 40 wt %, particularly preferably 0.01 to 20 wt %.

The application amount of the composition for external application to skin according to the present invention varies depending on the age, body weight, and degree of a disease of a test subject. The compound represented by the formula (I) or a salt thereof and/or the quaternary ammonium salt represented by the formula (II) is appropriately applied at a weight of, for example, 0.0002 mg to 100 mg, preferably 0.02 mg to 50 mg once a day or in their fractional amounts several times a day.

The composition for external application to skin according to the present invention is preferably at least one kind of composition selected from the group consisting of a photoaging-preventing composition, a photoaging-improving composition, a wrinkle-preventing composition, and a wrinkle-improving composition.

Evaluation of the photoaging-preventing action or wrinkle-preventing action and the photoaging-improving action or wrinkle-improving action of the composition for external application to skin according to the present invention is not particularly limited, and examples thereof include a method using wrinkle model animals such as hairless mice.

Hereinafter, methods for evaluating the photoaging- or wrinkle-preventing or photoaging- or wrinkle-improving action (effect) are described, but the present invention is not meant to be limited by them.

In evaluation of the photoaging-preventing action or wrinkle-preventing action, first, model animals are subjected to irradiation with ultraviolet rays such as UV-B, and immediately after that, the composition for external application to skin according to the present invention is applied. Subsequently, model animals applied with the composition for external application to skin according to the present invention are subjected to wrinkle score evaluation through visual evaluation of wrinkles, image analysis area ratio evaluation through image analyses of replicas, and skin elasticity measurement (details of the evaluation methods can be found in, for example, Bisselt et al., Photochem. Photobiol., 1989, 50, p. 763-769 and Tsukahara et al., Br. J. Dermatol., 2004, 151, p. 984-994). In such evaluation, in the case where significant inhibition of wrinkle formation is observed in model animals applied with the composition for external application to skin according to the present invention compared with model animals of negative control (for example, animals not applied with the composition for external application to skin according to the present invention or applied with a solvent), the composition for external application to skin according to the present invention can be evaluated to have a good photoaging-preventing or wrinkle-preventing action.

On the other hand, in evaluation of the photoaging-improving action or wrinkle-improving action, first, model animals are subjected to irradiation with ultraviolet rays such as UV-B to form wrinkles. Subsequently, the composition for external application to skin according to the present invention is applied to the wrinkle formation model animals. Subsequently, the wrinkle formation model animals applied with the composition for external application to skin according to the present invention are subjected to the above-mentioned wrinkle score evaluation, image analysis area ratio evaluation, and skin elasticity measurement. In such evaluation, in the case where a significant decrease in wrinkles is observed in the wrinkle formation model animals applied with the composition for external application to skin according to the present invention compared with wrinkle formation model animals of negative control (for example, animals not applied with the composition for external application to skin according to the present invention or applied with a solvent), the composition for external application to skin according to the present invention can be evaluated to have a good photoaging-improving action or wrinkle-improving action.

As described above, the composition for external application to skin according to the present invention has a sufficient photoaging-preventing or —improving action and/or wrinkle-preventing or —improving action. In particular, the composition for external application to skin according to the present invention has an action to prevent and improve deep and stubborn wrinkles (classification of wrinkles can be found in, for example, "Substantiation of Cosmetics Efficacy—Recent Progress and Future Promise—", Yakuji Nippo Ltd., 2001, chapter 1 section 7, p. 162-177; IMOKAWA Genji and TAKEMA Yoshinori, "Journal of Japanese Cosmetic Science Society", 1992, Vol. 16, No. 3, p. 153-155; and Genji Imokawa and Yoshinori Takema, "Cosmetics & Toiletries", 1993, Vol. 108, p. 65-77) formed in the muscles of facial expression and subcutaneous tissues by damages in the tissues of dermal cells or cells located deeper than the dermal cells.

Alverine described in Japanese Patent No. 3549823 is used as a muscle relaxant in Europe based on its acetylcholine-blocking action. Alverine has been used as a drug and has high toxicity (refer to, for example, David Malka et al., Journal of Hepathology, 1997, vol. 27, p. 399-403).

On the other hand, the compound represented by the above formula (I) or a salt thereof and the quaternary ammonium salt represented by the formula (II) in the composition for external application to skin according to the present invention are also considered to have an acetylcholine-blocking action. However, compared with alverine, the compound represented by the above formula (I) or a salt thereof and the quaternary ammonium salt represented by the formula (II) are metabolized in a human being in a short time (that is, easily detoxified) and have high safety.

According to the present invention, there is provided a composition for external application to skin having an action for fully preventing or improving photoaging and an action for fully preventing or improving wrinkles.

EXAMPLES

The present invention will be described in more detail based on examples given below, but the invention is not meant to be limited by these.

Synthesis Example 1

Synthesis of 2-dimethylamino-ethyl dodecanoate (Exemplified Compound (1))

2-dimethylamino-ethyl dodecanoate (Exemplified Compound (1)) was synthesized as follows.

Dimethylamino ethanol (10 g, 11.2 mmol) and chloroform (20 ml) were added to a 50-ml three-necked flask, and the whole was stirred and cooled to 5° C. in an ice bath. Subsequently, lauroyl chloride (2.5 g, 11.2 mmol) was added dropwise over 20 minutes. The resultant mixture was stirred in an ice bath for 0.5 hour and at room temperature for 2 hours, and the reaction was completed.

Sodium hydrogen carbonate (1.0 g, 11.8 mmol) and 10 ml of ion-exchange water were added to the resultant reaction mixture, and the whole was stirred at room temperature for 1 hour, followed by removal of the aqueous layer. The organic layer was washed with 10 ml of saturated saline and concentrated under reduced pressure, to thereby obtain an oily reaction mixture (1.4 g).

The resultant reaction mixture was subjected to silica gel column chromatography (silica gel 60, 30 g), and elution and concentration were performed with a chloroform/methanol mixed solvent (chloroform:methanol=100:1 to 1:1), to thereby obtain 2-dimethylamino-ethyl dodecanoate (1.2 g, yield 78.8%) as a colorless oil.

The resultant 2-dimethylamino-ethyl dodecanoate was subjected to a nuclear magnetic resonance (NMR) spectrum analysis and an infrared (IR) spectrum analysis, whereby the following results were obtained.

¹H-NMR (MeOH-d₄): 0.90 (t, 3H, J=7 Hz), 1.18-1.40 (m, 16H), 1.55-1.70 (m, 2H), 2.28 (s, 6H), 2.32 (t, 2H, J=7 Hz), 2.60 (t, 2H, J=6 Hz), 4.18 (t, 2H, J=6 Hz) ppm ¹³C-NMR (MeOH-d₄): 14.5, 23.7, 25.9, 30.2, 30.4, 30.5, 30.6, 30.7, 33.1, 34.9, 45.8, 58.6, 62.6, 174.9 ppm IR (NaCl): 3316, 2932, 2810, 2780, 2730, 1742, 1154 cm⁻¹

Synthesis Example 2

Synthesis of 2-dimethylamino-N-dodecyl-acetamide (Exemplified Compound (2))

2-Dimethylamino-N-dodecyl-acetamide (Exemplified Compound (2)) was synthesized as follows.

N,N-dimethylglycine methyl ester (1.50 g, 12.8 mmol) was added to n-dodecylamine (1.00 g, 5.4 mmol), and the whole was stirred at 150 to 160° C. for 5.5 hours. Then, the reaction was completed.

The mixture was allowed to stand to cool, and ethyl acetate (70 ml) and n-hexane (30 ml) were added. The impurities were subjected to filtration, and the filtrate was concentrated, to thereby obtain an oily product (1.4 g).

The resultant oily product was subjected to column chromatography, and elution was performed with a chloroform/methanol mixed solvent, to thereby obtain 2-dimethylamino-N-dodecyl-acetamide (1.27 g, yield 87.0%) as a pale yellow oily product.

The resultant 2-dimethylamino-N-dodecyl-acetamide was subjected to an NMR spectrum analysis and an IR spectrum analysis, whereby the following results were obtained.

¹H-NMR (DMSO-d₆) δ: 0.84 (t, 3H, J=6 Hz), 1.12-1.40 (m, 20H), 2.17 (s, 6H), 2.80 (s, 2H), 3.04 (q, 2H, J=7 Hz), 7.67 (t, 1H, J=6 Hz) ppm IR (ATR): 2923, 2853, 2777, 1660, 1520 cm⁻¹

Synthesis Example 3

Synthesis of dodecyl dimethylamino acetate (Exemplified Compound (3))

Dodecyl dimethylamino acetate (Exemplified Compound (3)) was synthesized as follows.

N,N-dimethylglycinemethyl ester (1.00 g, 5.6 mmol) and 28% sodium methoxide (0.11 g, 0.6 mmol) were added to n-dodecanol (3.16 g, 17.0 mmol), and the whole was stirred at 140 to 150° C. for 2.5 hours. Then, the reaction was completed.

The mixture was allowed to stand to cool, and the resultant mixture was subjected to extraction with ethyl acetate (70 ml), washed with water, and concentrated under reduced pressure, to thereby obtain an oily product (3.6 g).

The resultant oily product was subjected to column chromatography, and elution was performed with an ethyl acetate/n-hexane mixed solvent, to thereby obtain dodecyl dimethylamino acetate (1.18 g, yield 77.6%) as a pale yellow oily product.

The resultant dodecyl dimethylamino acetate was subjected to an NMR spectrum analysis and an IR spectrum analysis, whereby the following results were obtained.

¹H-NMR (DMSO-d₆) δ: 0.84 (t, 3H, J=7 Hz), 1.13-1.32 (m, 18H), 1.54 (qn, 2H, J=7 Hz), 2.22 (s, 6H), 3.12 (s, 2H), 4.01 (t, 2H, J=7 Hz) ppm IR (ATR): 2924, 2853, 2771, 1736, 1465 cm⁻¹

Synthesis Example 4

Synthesis of (2-dodecyloxy-ethyl)-dimethylamine (Exemplified Compound (4))

(2-dodecyloxy-ethyl)-dimethylamine (Exemplified Compound (4)) was synthesized as follows.

60% sodium hydride (0.47 g, 11.2 mmol) was added to a four-necked flask, and 50 ml of dry tetrahydrofuran were added at room temperature under a nitrogen stream, followed by stirring. Dimethylaminoethanol (1.00 g, 11.2 mmol), dissolved in dry tetrahydrofuran (10 ml), was added dropwise thereto over 20 minutes.

20 minutes after the addition, 1-bromododecane (2.80 g, 11.2 mmol), dissolved in dry tetrahydrofuran (5 ml), was added dropwise over 5 minutes. After completion of the addition, the mixture was heated to 50° C. and stirred for 4 hours, and the reaction was completed.

The mixture was allowed to stand to cool, and 20 ml of ion-exchange water was added to the reaction mixture. The whole was stirred well, and 100 ml of ethyl acetate was added, followed by extraction. The mixture was washed with water and concentrated under reduced pressure, to thereby obtain an oily product (2.68 g).

The resultant oily product was subjected to column chromatography, and elution was performed with a chloroform/methanol mixed solvent, to thereby obtain (2-dodecyloxy-ethyl)-dimethylamine (1.38 g, yield 47.9%) as a transparent oily product.

The resultant (2-dodecyloxy-ethyl)-dimethylamine was subjected to an NMR spectrum analysis and an IR spectrum analysis, whereby the following results were obtained.

¹H-NMR (CDCl₃) δ: 0.88 (t, 3H, J=7 Hz), 1.16-1.54 (m, 18H), 1.58 (qn, 2H, J=6 Hz), 2.27 (s, 6H), 2.50 (t, 2H, J=6 Hz), 3.42 (t, 2H, J=7 Hz), 3.51 (t, 2H, J=6 Hz) ppm IR (ATR): 2956, 2915, 2850, 1470, 1120 cm⁻¹

Synthesis Example 5

Synthesis of (2-dimethylaminoethyl)-amide dodecanoate (Exemplified Compound (5))

(2-dimethylaminoethyl)-amide dodecanoate (Exemplified Compound (5)) was synthesized as follows.

N,N-dimethylethylenediamine (1.00 g, 11.3 mmol) was dissolved in chloroform (50 ml), and the whole was cooled to 5° C. Subsequently, dodecyl chloride (2.45 g, 11.2 mmol) was added dropwise over 10 minutes.

After completion of the addition, the temperature of the mixture was returned to room temperature, and the resultant mixture was stirred for 2 hours. After completion of the reaction, the reaction mixture was concentrated under reduced pressure, and the residue was subjected to extraction with ethyl acetate (150 ml). After the extraction, an aqueous solution of saturated sodium hydrogen carbonate (50 ml) was added to wash the mixture, and the mixture was washed with saturated saline (50 ml) and concentrated under reduced pressure, to thereby obtain white solids (2.99 g).

Ion-exchange water (13 ml) was added to the resultant white solid, and the whole was stirred at 60° C. for 30 minutes. The impurities were subjected to filtration, and the filtrate was cooled to 5° C. After the cooling, the resultant crystals were subjected to filtration and dried at 40° C. for 12 hours, to thereby obtain (2-dimethylaminoethyl)-amide dodecanoate (2.45 g, yield 79.5%) as white crystals.

The melting point of the resultant (2-dimethylaminoethyl)-amide dodecanoate was found to be 47.7 to 48.3° C. Moreover, the resultant (2-dimethylaminoethyl)-amide dodecanoate was subjected to an NMR spectrum analysis and an IR spectrum analysis, whereby the following results were obtained.

$^1$H-NMR (DMSO-$d_6$) δ: 0.84 (t, 3H, J=7 Hz), 1.12-1.32 (m, 16H), 1.44 (qn, 2H, J=7 Hz), 2.02 (t, 2H, J=7 Hz), 2.12 (s, 6H), 2.23 (t, 2H, J=6 Hz), 3.10 (q, 2H, J=6 Hz), 7.68 (t, 1H, J=7 Hz)

IR (ATR): 2916, 2847, 2820, 1637, 1550 cm$^{-1}$

Synthesis Example 6

Synthesis of 2-dimethylamino-N-ethyl-acetamide (Exemplified Compound (6))

2-dimethylamino-N-ethyl-acetamide (Exemplified Compound (6)) was synthesized as follows.

N,N-dimethylglycine (0.8 g, 6.8 mmol) was dissolved in an aqueous solution of 70% ethylamine (5.7 g, 68 mmol), and the solution was placed in a closed vessel and stored at 5° C. for 3 days. The solution was concentrated under reduced pressure, and the resultant oily product was subjected to column chromatography, followed by extraction with a chloroform/methanol mixed solvent, to thereby obtain Exemplified Compound (6) (0.84 g, 94.4%) as a colorless oil.

The resultant Exemplified Compound (6) was subjected to an NMR spectrum analysis and an IR spectrum analysis, whereby the following results were obtained.

$^1$H-NMR (DMSO-$d_6$) δ: 0.99 (t, 3H, J=7 Hz), 2.20 (s, 6H), 2.80 (s, 2H), 3.10 (q, 2H, J=7 Hz), 7.73 (br. s, 1H)

IR (ATR): 2973, 2824, 2778, 1651, 1522 cm$^{-1}$

Synthesis Example 7

Synthesis of dodecylcarbamoylmethyl trimethylammonium chloride (Exemplified Compound (7))

Dodecylcarbamoylmethyl trimethylammonium chloride (Exemplified Compound (7)) was synthesized as follows.

60.0 g (0.32 mol) of n-dodecylamine were dissolved in 900 ml of chloroform, and 43.2 g (0.43 mol) of triethylamine were added, followed by cooling to −50° C. 40.2 g (35.6 mol) of chloroacetyl chloride was added dropwise over 30 minutes while the temperature was maintained, and the mixture was further stirred for 1 hour while the temperature was maintained. Then, the reaction was completed. 100 ml of ethanol was added to the reaction mixture, and 300 ml of ion-exchange water was added. The mixture was heated to room temperature and stirred for 20 minutes, and the whole was allowed to stand to separate the layers. The lower layer was concentrated, and the residue was subjected to silica gel column chromatography, followed by extraction with a chloroform-methanol mixed solvent. The solvent was distilled off, to thereby obtain 85.3 g of a residue.

60.27 g of the residue was charged to a stainless-steel simple autoclave, and a solution of trimethylamine in 33% ethanol and 180 ml of ethanol were added, followed by sealing. The mixture was heated to 100 to 110° C. in an oil bath and stirred for 5 hours, and the reaction was completed. The mixture was cooled to room temperature, and the pressure was reduced. The reaction solution was concentrated, and the residue was subjected to silica gel column chromatography, followed by elution with a chloroform-methanol mixed solvent. The solvent was distilled off, and the residue was recrystallized with ethanol-n-hexane, to thereby obtain Exemplified Compound (7) (55.8 g, yield 54.3%) as white needle crystals.

The resultant Exemplified Compound (7) was subjected to an NMR spectrum analysis and an IR spectrum analysis, whereby the following results were obtained.

$^1$H-NMR (CDCl$_3$) δ: 0.88 (t, 3H, J=7 Hz), 1.25-1.31 (m, 18H), 1.57 (qn, 2H, J=7 Hz), 3.25 (q, 2H, J=6 Hz), 3.49 (s, 9H), 4.70 (s, 2H), 9.22 (t, 1H, J=5 Hz)

Example 1

Evaluation of photoaging- and wrinkle-preventing effect using composition according to the present invention (1) Preparation of Wrinkle Model Animal (Hairless Mouse)

Six-week-old ICR/HR female mice prepared by mating HR/HR mice with HaM/ICR mice were used as wrinkle model animals (wrinkle-formed hairless mice). The mice were allowed to take feed and water freely and raised in an ultraviolet-free environment of a temperature of 23° C. and a humidity of 55%.

(2) Evaluation of Photoaging- and Wrinkle-preventing Action (i) Conditions of Ultraviolet Ray Irradiation The hairless mice raised as above were divided into 7 groups each having 8 mice and were irradiated with UV-B. UV-B irradiation was performed according to a known general method described in Tsukahara et al. (Br. J. Dermatol., 2004, 151, p. 984-994) or the like. Specifically, the hairless mice raised as above were placed in cages and irradiated with UV-B using Toshiba SE lamps. Irradiation was performed at an irradiance level of 40 to 50 mJ/cm$^2$, which corresponds to 0.8 to 1 MED (minimal erythema dose) for general 6-week-old hairless mice, over 12 weeks five times a week.

(ii) Preparation and Application of Samples

Samples to be applied to the hairless mice were prepared as 1% Exemplified Compound (1)/90% ethanol (EtOH) solution, 3% Exemplified Compound (1)/90% EtOH solution, 1% Exemplified Compound (2)/90% EtOH solution, 1% Exemplified Compound (3)/90% EtOH solution, 0.1% Exemplified Compound (4)/90% EtOH solution, and 1% Exemplified Compound (5)/90% EtOH solution.

Immediately after the ultraviolet ray irradiation, 90% EtOH (control) and the samples prepared as above were applied to the hairless mice of the respective groups over 12 weeks with five times a week at a dose of 100 µL/day. The groups of the hairless mice applied with the samples include "90% EtOH control group" consisting of the mice applied with 90% EtOH, "1%-compound 1 group" consisting of the mice applied with 1% Exemplified Compound (1)/90% EtOH solution, "3%-compound 1 group" consisting of the mice applied with 3% Exemplified Compound (1)/90% EtOH solution, "1%-compound 2 group" consisting of the mice applied with 1% Exemplified Compound (2)/90% EtOH solution, "1%-compound 3 group" consisting of the mice applied with 1% Exemplified Compound (3)/90% EtOH solution, "0.1%-compound 4 group" consisting of the mice applied with 0.1% Exemplified Compound (4)/90% EtOH solution, and "1%-compound 5 group" consisting of the mice applied with 1% Exemplified Compound (5)/90% EtOH solution.

(iii) Evaluation of Wrinkle-preventing Effect (Visual Evaluation of Wrinkles)

Five-grade evaluation for wrinkles was performed to classify wrinkles into grades 0 to 4 by reference to the method described in Bissett et al. (Photochem. Photobiol., 1989, 50, p. 763-769) by a known method described in Tsukahara et al. (Br. J. Dermatol., 2004, 151, p. 984-994) or the like.

The score of the 90% EtOH control group was defined as 100, and wrinkle scores of the respective groups were evaluated based on the five-grade evaluation.

(iv) Preparation of Replica and Image Analysis

Replica collection and image analysis were performed as described below. A replica was collected from the skin of the back of each hairless mouse using a rubber-based silicon impression material (GC Corporation) by a known method described in Tsukahara K et al. (Br. J. Dermatol., 2004, 151, p. 984-994) or the like.

The collected replicas were cut out into pieces with a diameter of 1.8 cm, and the pieces were lined with the impression material to correct the pieces and subjected to an image analysis. The image analysis was performed using PIAS LA-555 (PIAS Corporation) by irradiating each piece with light from a direction of oblique 30 degrees to quantify shadows formed in an area of 10 mm×10 mm (image analysis area ratio (%)).

The image analysis area ratio of the 90% EtOH control group was defined as 100, and the image analysis area ratios (%) of the respective groups were evaluated based on the image analysis area ratios obtained by the quantification.

(v) Measurement of Skin Elasticity

Measurement of skin elasticity was performed by a known method described in Tsukahara K et al. (Br. J. Dermatol., 2004, 151, p. 984-994) using Cutometer SEM575 (C+K Corporation) to measure a displacement formed in 2 seconds in total with a 1-second suction of 100 mb, followed by a 1-second relaxation period. Measurement was performed five times for each mouse to determine Ue, which is a parameter of an instantaneous elasticity displacement. The Ue value of the 90% EtOH control group was defined as 100, and Ue values of the respective groups were determined.

(vi) Results (a) Results of Evaluation of Wrinkle-Preventing Effect (Visual Evaluation of wrinkles)

The results of evaluation of wrinkle-preventing effect (visual evaluation of wrinkles) are shown in FIG. 1.

As shown in FIG. 1, application of the composition for external application to skin of the present invention was found to inhibit increases in the wrinkle scores. In the case of the 1%-compound 5 group, the maximum effect of inhibiting wrinkle formation was observed. Moreover, the wrinkle formation inhibiting effects of the 1%-compound 3 group, 1%-compound 1 group, 3%-compound 1 group, 1%-compound 2 group, and 0.1%-compound 4 group were found to decrease in this order.

(b) Results of Replica Image Analysis

Figure 2:
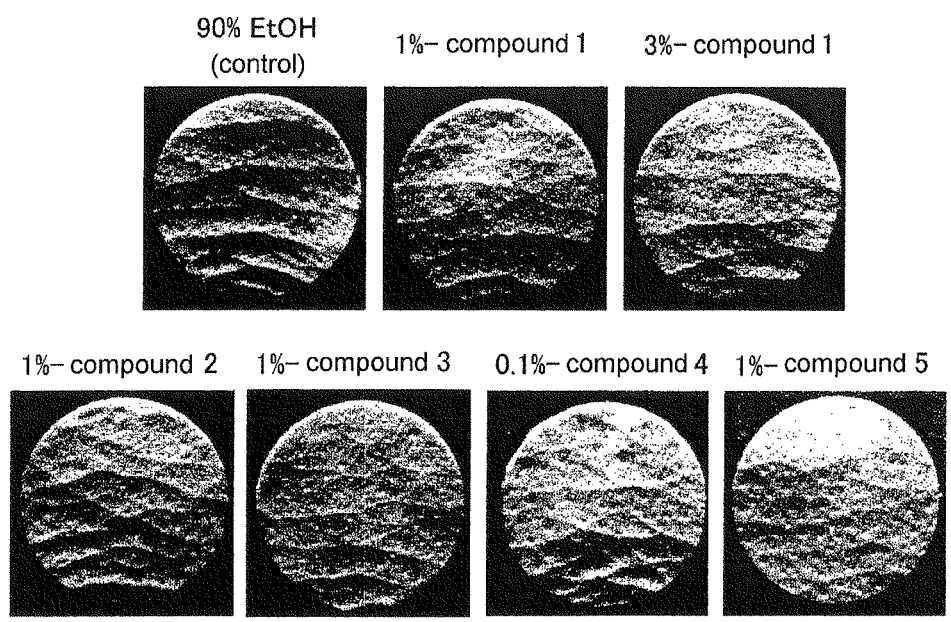
FIG. 2 are photographs showing the replicas of respective groups in Example 1.

FIG. 2 shows photographs of the replicas of the respective groups. In addition, FIG. 3 shows the results of the replica image analysis.

Figure 3:
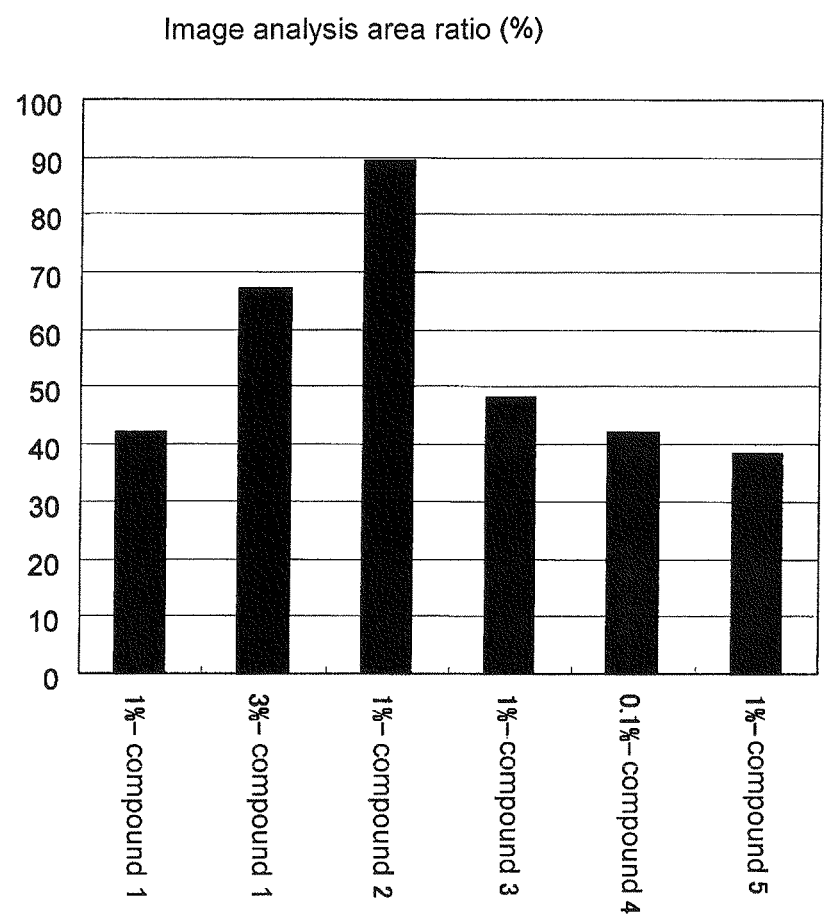
FIG. 3 is a graph illustrating the results of replica image analysis in Example 1.

As shown in FIGS. 2 and 3, application of the composition for external application to skin of the present invention was found to inhibit increases in wrinkles. In the case of the 1%-compound 5 group, the maximum effect of inhibiting wrinkle formation was observed. Moreover, the wrinkle formation inhibiting effects of the 1%-compound 1 group, 0.1%-compound 4 group, 1%-compound 3 group, 3%-compound 1 group, and 1%-compound 2 group were found to decrease in this order.

(c) Results of Measurement of Skin Elasticity

Figure 4:
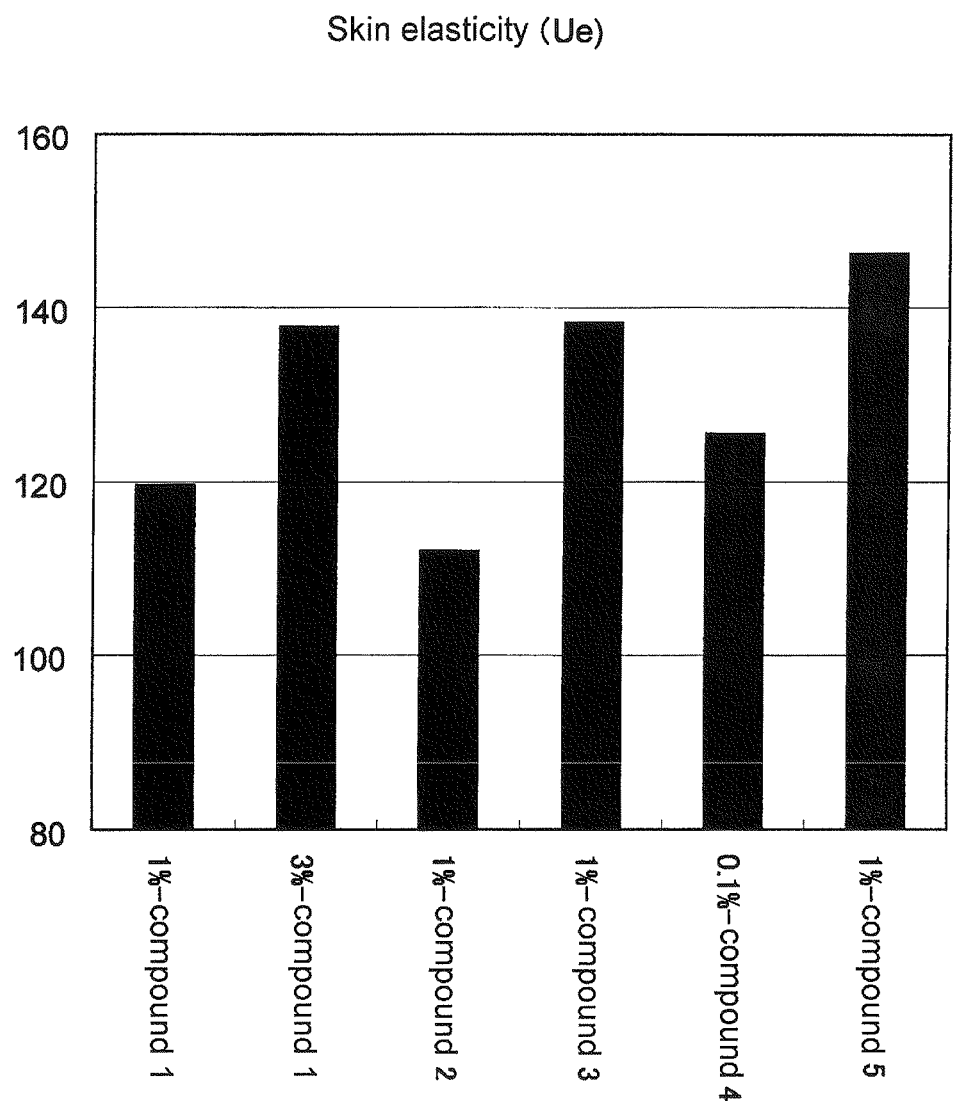
FIG. 4 is a graph illustrating the results of skin elasticity measurement in Example 1.

The results of measurement of skin elasticity are shown in FIG. 4.

As shown in FIG. 4, application of the composition for external application to skin of the present invention was found to inhibit the decrease in skin elasticity. In the case of the 1%-compound 5 group, the maximum effect of inhibiting the decrease in skin elasticity was observed. Moreover, the effects of inhibiting the decrease in skin elasticity of the 1%-compound 3 group, 3%-compound 1 group, 0.1%-compound 4 group, 1%-compound 1 group, and 1%-compound 2 group were found to decrease in this order.

(vii) Comprehensive Evaluation

The composition for external application to skin of the present invention was found to have a photoaging-preventing and wrinkle-preventing effect. In addition, in the cases of the 1% and 3% compound 1, 1% compound 2, 1% compound 3, 0.1% compound 4, and 1% compound 5, the photoaging-preventing and wrinkle-preventing effects were found to be high.

Example 2

Evaluation of Wrinkle-improving Effect by Composition According to Present Invention (1) Preparation of Wrinkle-formed Hairless Mice Wrinkle-formed hairless mice were prepared according to the description in the sections (1) and (2)(ii) of the above Example 1 by irradiating 6-week-old ICR/HR female mice, prepared by mating HR/HR with HaM/ICR, with UV-B over 10 weeks five times a week.

The hairless mice having wrinkles formed by irradiation with UV-B were visually evaluated with reference to the method described in Bisselt et al. (Photochem. Photobiol., 1989, 50, p. 763-769) by a known method described in Tsukahara et al. (Br. J. Dermatol., 2004, 151, p. 984-994) to divide the mice into two groups each having eight mice so that the average values of wrinkle scores (evaluated according to the description in the section 2)(iii) of Example 2)(iii)) of the respective groups were almost the same.

(2) Evaluation of Wrinkle-improving Effect (i) Preparation and Application of Samples A sample to be applied to the wrinkle-formed hairless mice was prepared as 1% compound (1)/90% EtOH solution.

The 90% EtOH (control) and the sample prepared as above were applied to the wrinkle-formed hairless mice of the respective groups over 6 weeks with five times a week at a dose of 100 μday. The groups of the wrinkle-formed hairless mice applied with the samples include "90% EtOH control group" consisting of the mice applied with 90% EtOH, and "1%-compound 1 group" consisting of the mice applied with 1% Exemplified Compound (1)/90% EtOH solution.

(ii) Evaluation of Wrinkle-improving Effect (Visual Evaluation of Wrinkles)

Five-grade evaluation for wrinkles was performed to classify wrinkles into grades 0 to 4 according to the description in the section (2) (iii) of Example 1.

(iii) Results

Figure 5:
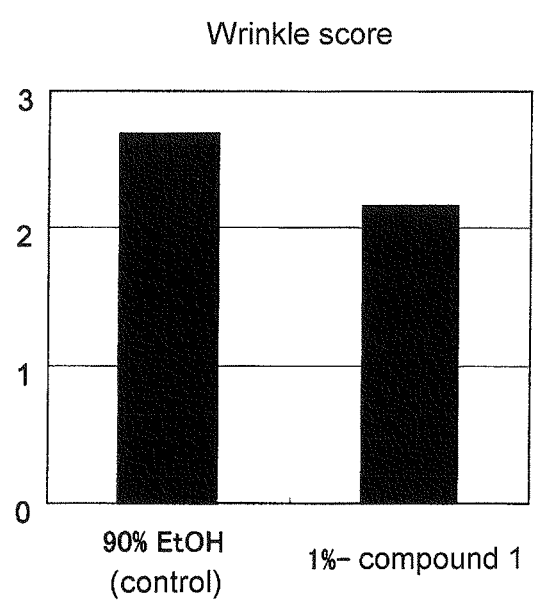
FIG. 5 is a graph illustrating the results of evaluation of wrinkle-improving effect (visual evaluation of wrinkles) in Example 2.

The results of evaluation of wrinkle-improving effect (visual evaluation of wrinkles) are shown in FIG. 5.

As shown in FIG. 5, the wrinkle score of the 1%-compound 1 group was found to be lower than that of the 90% EtOH control group.

(iv) Comprehensive Evaluation

The composition for external application to skin of the present invention was found to have an effect of improving (decreasing) wrinkles formed by irradiation with UV-B.

Formulation Example

A lotion, cream, aerosol, pack, foundation, skin lotion, and gel having the following components were prepared through a conventional method using a compound represented by the above formula (I) or a salt thereof, and/or, a quaternary ammonium salt represented by the above formula (II) as an active ingredient.

1. Preparation of Lotion

The following components were mixed to prepare liquid A1. In addition, the following components were mixed to prepare liquid B1. B1 was added to A1, and the whole was mixed uniformly by stirring, to thereby obtain a lotion.

Components of A1

| (Component) | (Content: mass %) |
| --- | --- |
| Polyoxyethylene hardened castor oil | 0.8 |
| Ethanol | 30.0 |

Components of B1

| (Component) | (Content: mass %) |
| --- | --- |
| Exemplified compound (1) | 1.0 |
| Sodium dodecylsulfate | 0.12 |
| Dodecylmethylamine oxide | 0.18 |
| Isopropyl alcohol | 15.0 |
| Benzyl alcohol | 15.0 |
| Glycerol | 2.0 |
| Purified water | Balance |

2. Preparation of Cream

The following components were mixed to prepare liquid A2. In addition, the following components were mixed to prepare liquid B2. B2 was added to A2, and the whole was mixed uniformly by stirring to emulsify the mixture and cooled, to thereby obtain a cream.

Components of A2

| (Component) | (Content: mass %) |
| --- | --- |
| Liquid paraffin | 10.0 |
| Squalane | 7.0 |
| Jojoba oil | 3.0 |
| Solid paraffin | 3.0 |
| Polyoxyethylene cetyl ether | 2.0 |
| Sorbitan sesquioleate | 1.0 |
| Potassium hydroxide | 0.1 |

Components of B2

| (Component) | (Content: mass %) |
| --- | --- |
| Exemplified compound (1) | 1.0 |
| Glycerol | 3.0 |
| Ethylparaben | 0.1 |
| Purified water | Balance |

3. Preparation of Aerosol

Exemplified Compound (5), cetanol, propylene glycol, ethanol, and purified water shown below were mixed uniformly and placed in a container, and the container was filled with a liquefied petroleum gas (propellant) through a conventional method, to thereby produce an aerosol.

| (Component) | (Content: mass %) |
| --- | --- |
| Exemplified compound (5) | 1.0 |
| Cetanol | 1.2 |
| Propylene glycol | 4.0 |
| Ethanol | 8.0 |
| Purified water | Balance |
| Liquefied petroleum gas (propellant) | 4.0 |

4. Preparation of Pack

A pack having the following components was prepared through a conventional method.

| (Component) | (Content: mass %) |
| --- | --- |
| Exemplified compound (3) | 3.0 |
| Polyvinyl alcohol | 20.0 |
| Glycerin | 5.0 |
| Ethanol | 16.0 |
| Perfume | Trace |
| Dye | Trace |
| Purified water | Balance |

5. Preparation of Foundation

A foundation having the following components was prepared through a conventional method.

| (Component) | (Content: mass %) |
| --- | --- |
| Exemplified compound (1) | 1.0 |
| Spherical silica beads | 20.0 |
| Silica coated sericite | 45.0 |
| Titanium oxide ultrafine particle | 10.0 |
| Yellow iron oxide | 3.0 |
| Talc | 5.0 |
| Mica | 5.0 |
| Colcothar | 1.0 |
| Ultramarine | 1.0 |
| Paraben | 0.2 |
| Liquid paraffin | 4.8 |
| Squalane | 4.0 |

6. Preparation of Skin Lotion

A skin lotion having the following components was prepared through a conventional method.

| (Component) | (Content: mass %) |
| --- | --- |
| Exemplified compound (1) | 5.0 |
| Exemplified compound (3) | 0.5 |
| Glycerol | 15.0 |
| Dipropylene glycol | 5.0 |
| Purified water | Balance |

7. Preparation of Gel

A gel having the following components was prepared through a conventional method.

| (Component) | (Content: mass %) |
| --- | --- |
| Polyacrylic acid | 0.5 |
| Potassium hydroxide | 0.15 |
| Glucam | 10.0 |
| Glycerol | 10.0 |
| Glycinebetaine | 3.0 |
| Exemplified compound (3) | 2.0 |
| Succinic acid | 1.5 |
| Purified water | Balance |

INDUSTRIAL APPLICABILITY

The composition containing a compound represented by the above formula (I) or a salt thereof and/or a quaternary ammonium salt represented by the above formula (II) has an action of preventing or improving appearance changes (such as wrinkles and sagging) or reduction of skin firmness, which are both caused by skin aging. Therefore, the composition for external application to skin according to the present invention is useful as a photoaging-preventing composition, a photoaging-improving composition, a wrinkle-preventing composition, and/or a wrinkle-improving composition.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2007-294763 filed in Japan on Nov. 13, 2007, of which is entirely herein incorporated by reference.

The invention claimed is:

1. A method for preventing photoaging of wrinkled skin or improving photoaging of wrinkled skin, comprising externally applying a composition that comprises a compound represented by formula (I) or a salt thereof:

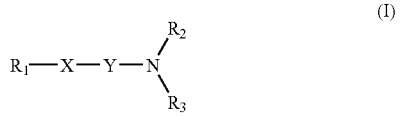

(I)

wherein, in formula (I), $R_1$ is an unsubstituted, linear chain alkyl group having 10 to 14 carbon atoms; X is —CO—NH—, —O—CO—O—, —NH—CO—, or —O—; Y is an unsubstituted alkylene group having 1 to 4 carbon atoms; $R_2$ is a hydrogen atom or an alkyl group having 1 to 4 carbon atoms; and $R_3$ is an alkyl group having 1 to 4 carbon atoms;

to the wrinkled skin of a subject in need of prevention or improvement of photoaging of said skin, and preventing or improving said photoaging of said skin as a result of said applying.

2. The method according to claim 1, wherein X is —CO—NH— or —NH—CO—.

3. The method according to claim 1, wherein Y is a methylene group or an ethylene group.

4. The method according to claim 1, wherein $R_2$ is a hydrogen atom, a methyl group, or an ethyl group and $R_3$ is a methyl group or an ethyl group.

5. The method according to claim 1, wherein the compound represented by the above formula (I) is a compound selected from the group consisting of 2-dimethylamino-N-dodecyl-acetamide, dodecyl dimethylamino acetate, (2-dodecyloxy-ethyl)-dimethylamine, and (2-dimethylaminoethyl)amide dodecanoate.

6. The method of claim 1, wherein said $R_2$ and $R_3$ are the same.

7. The method of claim 1, wherein said $R_2$ and $R_3$ are different.

8. The method of claim 5, wherein said $R_2$ and $R_3$ are the same.

9. The method of claim 5, wherein said $R_2$ and $R_3$ are different.

10. The method of claim 1, wherein the wrinkled skin is on the face.

* * * * *